United States Patent [19]

Dalton, Jr. et al.

[11] 4,225,694

[45] Sep. 30, 1980

[54] SELECTIVE CATALYTIC OXIDATION OF UNSATURATED ALCOHOLS TO CARBONYL COMPOUNDS

[75] Inventors: Augustine I. Dalton, Jr., Allentown, Pa.; Henry J. Doran, Bray, Ireland; Robert D. H. Murray, Glasgow, Scotland

[73] Assignee: Air Products and Chemicals, Inc., Allentown, Pa.

[21] Appl. No.: 830,405

[22] Filed: Sep. 6, 1977

Related U.S. Application Data

[63] Continuation-in-part of Ser. No. 616,260, Sep. 24, 1975, abandoned.

[51] Int. Cl.$^2$ .................... C07C 51/32; C07C 61/18; C07C 63/06
[52] U.S. Cl. ..................... 562/506; 260/413; 562/418; 562/419; 562/503; 562/505; 562/510; 562/533; 562/538; 568/363; 568/403; 568/420; 568/437; 568/485
[58] Field of Search ........... 260/514 H, 531 R, 515 R, 260/413, 586 P, 596, 590 R, 603 C, 598, 599; 562/506, 538, 419, 418, 503, 505, 510, 533

[56] References Cited

U.S. PATENT DOCUMENTS 3,479,403 11/1969 MacLean ............................. 562/534
3,997,578 12/1976 Sheng ............................. 260/531 R

OTHER PUBLICATIONS

Roberts et al., Basic Principles of Org. Chem., 1965, pp. 99, 111-114, 125 & 141.
Smejkae et al., Coll. Czech. Chem. Comm., 38, 1973, p. 1981.
Fatiadi, Synthesis, #4, 1974, p. 229.
Mills et al., J. Chem. Soc. (Perkin I), 1973, p. 133.
Spitzer et al., J. Org. Chem., 39, No. 16, 1974, pp. 2468 & 2539.
Lee et al., Canadian J. of Chem., vol. 50, pp. 3741-3743 (1972).
Rylander, Org. Syn. with Noble Metal Catalysts, vol. 28, 1973, pp. 133-134 and 136.

*Primary Examiner*—Vivian Garner
*Attorney, Agent, or Firm*—Richard A. Dannells, Jr.; Barry Moyerman

[57] ABSTRACT

Primary and secondary unsaturated alcohols are converted to their corresponding aldehydes and/or carboxylic acids and ketones respectively with alkali metal (per) halate, preferably sodium periodate, in the presence of ruthenium catalyst. The process is particularly useful in the oxidation of chrysanthemyl alcohol. Any unconverted intermediate aldehyde formed may be converted to the acid by recycling or by a separate oxidation step.

6 Claims, No Drawings

SELECTIVE CATALYTIC OXIDATION OF UNSATURATED ALCOHOLS TO CARBONYL COMPOUNDS

CROSS-REFERENCE TO RELATED APPLICATIONS

This application is a continuation-in-part of application Ser. No. 616,260, filed Sept. 24, 1975, abandoned.

BACKGROUND OF THE INVENTION

1. Field of the Invention

The present invention is concerned generally with the conversion of labile primary and secondary unsaturated alcohols to their corresponding aldehydes and/or carboxylic acids and ketones respectively and more particularly with the production of chrysanthemic acid from the corresponding alcohol.

2. Description of the Prior Art

There are few general and inexpensive methods known for oxidation of labile primary alcohols selectively to aldehydes and/or acids. Lee, D. G. et al, in *Can. J. Chem.* vol 50, pages 3741 et seq. (1972) describe the use of sodium ruthenate ($Na_2RuO_4$) as a reagent for oxidation of primary or secondary alcohols to the carboxy acids or ketone respectively. This process is not attractive for large scale operation in that a two step procedure is generally necessary for production of the acid and furthermore involves the use of highly expensive sodium ruthenate in stoichiometric quantity as oxidizing agent. This reagent cannot be efficiently employed as oxidizing agent for the oxidation of alcohols containing functional components that are sensitive to strong oxidizing agents, nor for oxidation of unsaturated alcohols which require elevated temperature and/or extended reaction time, since under these conditions the ruthenate attacks the carbon-carbon double bond with loss of yield of the desired unsaturated acid.

It has also been recently disclosed that in aqueous acetone, the primary alcohol function of sugars can be oxidized to the acid in low yield by an in situ combination of ruthenium tetroxide ($RuO_4$) in catalytic amount with sodium periodate ($NaIO_4$); Smejkae, J. et al, *Coll. Czech. Chem. Comm.*, 38, 1981 (1973). It is known, on the other hand, however, that $RuO_4$ attacks alkenes to form glycols which in turn are cleaved by $NaIO_4$, so that the utility of this reagent for application to oxidation of unsaturated alcohols appears to be limited (Fatiadi, A. I., Synthesis, #4, 229 (1974)).

For the oxidation of chrysanthemyl alcohol to the corresponding carboxylic acid, it has hitherto been proposed to employ chromium trioxide in pyridine. (Published German Application OLS No. 2,164,024) see also Mills, R. W. et al, *Jour. Chem. Soc. (Perkin I)*, 133 (1973). This process requires relatively long reaction periods for ultimate conversion of the intermediate aldehyde formed to the desired carboxy acid, which is obtained in only moderate yield.

SUMMARY OF THE INVENTION

In accordance with the present invention, a relatively inexpensive and simplified method is provided generally useful in conversion of labile primary or secondary unsaturated alcohols to their corresponding carboxylic acids or ketones. This method moreover, is applicable to more difficultly oxidizable alcohols containing olefinic unsaturation and sensitive functional groups such as chrysanthemyl alcohol, which alcohols are oxidized, in accordance with the invention, to the corresponding carboxylic acids, in high yields.

The oxidation of the alcohol is carried out by the method of the present invention employing only a catalytic amount of ruthenium oxide or alkali metal ruthenate in aqueous alkaline medium with a substantially stoichiometric amount of a co-oxidation catalyst of sufficiently high potential such as certain alkali metal (per) halates, to continually regenerate the alkali metal ruthenate throughout the oxidation reaction.

The reaction mechanism is believed, in the case of primary alcohols, to involve intermediate conversion of the alcohol to aldehyde and in situ further oxidation of the aldehyde to the corresponding carboxylic acid. The oxidation of the alcohol to the aldehyde (or ketone in the case of a secondary alcohol) is relatively rapid as compared to the subsequent stage of the reaction, formation of the acid. In accordance with an alternative embodiment of the invention, the second stage reaction can be accelerated by addition of other oxidizing agents promoting conversion of the aldehyde intermediate to the acid, thereby increasing the rate of the overall oxidative transformation.

The operation of the invention will be understood and additional advantages thereof appreciated from the detailed description which follows in the examples below illustrating certain preferred embodiments thereof without limitation thereto. While the examples illustrate oxidation of chrysanthemyl alcohol to the acid, it will be appreciated that this alcohol contains the alkene, cyclopropyl, cyclopropylcarbinol and allylic hydrogen functionalities which frequently are sensitive to oxidizing media. It is evident, therefore, that less sensitive alcohols, will be successfully oxidized by practice of the invention, with the exclusion, perhaps, of those alcohols also containing an amine function.

It follows from the foregoing that the primary and secondary alcohols contemplated for oxidation by the process of the present invention include:

(1) olefinically unsaturated alcohols selected from the group consisting of straight or branched chain alcohols preferably having up to 25 carbon atoms and cycloalkyl containing alcohols preferably having 3 to 8 carbon atoms and still more preferably having 3 to 6 carbon atoms; and (2) aromatically unsaturated alcohols which contain an aryl alkyl functionality preferably having up to 25 carbon atoms.

EXAMPLE 1

To 6 parts by weight of chrysanthemyl alcohol (40 m mol) in 1 molar aqueous NaOH (30 grams alcohol/liter of alkaline solution) there were added 18 parts of sodium periodate (84 m mol) and 0.1 parts (0.75 m mol) ruthenium dioxide. An orange-red mixture was obtained.

After stirring the obtained mixture for 22 hours at room temperature, it turned black. The mixture was filtered and the aqueous alkali filtrate was washed with ether, yielding 1.4 parts of a neutral fraction consisting of unreacted alcohol and some chrysanthemyl aldehyde.

The aqueous alkali phase was acidified with sulfuric acid and extracted with ether. There was obtained 4.3 parts chyrsanthemic acid, constituting an overall yield of 64%, at approximately 77% conversion of the alcohol. The selectivity to acid thus was 83%.

To obtain acceptable yields of desired acid, the ruthenium oxide catalyst (RuO$_2$) should be employed generally in an amount corresponding to at least about 0.5 mols per 100 mols of the alcohol and up to about 10 mols per hundred of the alcohol. While greater amounts of the catalyst can be employed, this would add no useful advantage. With amounts of RuO$_2$ considerably below this proportion, the selectivity and total yield of acid are substantially lower, as will be seen from Example 2 below.

EXAMPLE 2

The run described in Example 1 above was repeated with the use of only 0.006 parts by weight RuO$_2$; (0.11 mols RuO$_2$ per 100 mols alcohol).

The reaction was allowed to proceed for 1 hour at 60° C. After work-up of the reaction product as described in the preceding example, there was obtained 1.6 parts of a neutral material comprising unreacted starting alcohol and aldehyde, and 3.4 parts of a mixture of chrysanthemic and caronic acid.

EXAMPLE 3

The effect of employing the alkali at higher concentration is seen from the following run.

The reactants were the same as in Example 1 above, except that the starting alcohol was dissolved in 5 molar aqueous NaOH, employing 27.5 grams alcohol per liter of the aqueous alkaline solution. After reaction for one hour, the reaction mixture was diluted by addition of 62.5% water by volume of the original aqueous alkaline solution, and the reaction permitted to continue at room temperature for 17 hours.

The reaction mixture was worked up as described in Example 1 above, yielding 1.6 parts of a mixture of starting alcohol and chrysanthemyl aldehyde, and 5 parts of a product consisting primarily of chrysanthemic acid.

Instead of employing RuO$_2$ with the alkali metal periodate one can employ a catalytic quantity of sodium ruthenate (Na$_2$RuO$_4$). It is believed, that RuO$_2$ is formed in situ in the reaction, and in turn is oxidized by the periodate thereby, in the presence of alkali, regenerating the ruthenate. The direct use of the sodium ruthenate as catalyst is illustrated in the following examples.

EXAMPLE 4

To 1.2 parts by weight (8 m mols) chrysanthemyl alcohol in 1 molar aqueous NaOH (12 grams alcohol per liter of alkaline solution), there were added 4 parts (18 m mol) NaIO$_4$ and 0.4 m mol Na$_2$RuO$_4$. After stirring for five hours at room temperature, an aliquot portion of the reaction product was analyzed and found to contain chrysanthemyl aldehyde and chrysanthemic acid but no starting alcohol.

The product was filtered to remove solids and the filtrate stirred overnight. The reaction product was worked up in the manner above described (Example 1) with the recovery of 0.2 parts of a neutral fraction composed principally of chrysanthemyl alcohol and 0.9 parts of chrysanthemic acid.

EXAMPLE 5

To 6 parts by weight chrysanthemyl alcohol (40 m mol) in 1 molar/aqueous NaOH (20 grams alcohol/liter aqueous NaOH) there were added 20 parts NaIO$_4$ (90 m mol) and 2 m mol Na$_2$RuO$_4$ (5 mol % on alcohol).

The reaction mixture was stirred for 23 hours at room temperature. After work up in the manner before described (Example 1) there was obtained 0.6 parts of a neutral product consisting primarily of chrysanthemyl aldehyde, and 4 parts of chrysanthemic acid.

Conversion of the aldehyde to obtain additional yields of acid may be effected by separating the aldehyde from the acid by extraction or in other known manner, and recycling the aldehyde to the principal reaction for further conversion over the ruthenium catalyst. More rapid conversion of the aldehyde to the corresponding carboxylic acid can be obtained by subjecting the same to a separate oxidation step such as by reaction with silver oxide or by catalytic oxidation with air or other oxygen containing gas, employing for example silver oxide as catalyst promoted with copper oxide by the method described in Belgian Patent Nos. 656,905 of Apr. 1, 1965 and 657,745 of Apr. 30, 1965. These methods for oxidation of chrysanthemyl aldehyde to chrysanthemic acid are described more fully and claimed in application Ser. No. 616,405 filed on Sept. 24, 1975, now U.S. Pat. No. 4,049,706.

In the foregoing examples, sodium periodate (NaIO$_4$) was employed as the oxidizing agent. Since RuO$_2$ would likewise be oxidized to alkali metal ruthenate in the presence of alkali and other co-oxidants of sufficient oxidation potential, halites such as sodium hypochlorite and halates such as sodium bromate, these may in certain instances be substituted for the sodium periodate. The advantageous choice of the co-oxidant to the ruthenium substrate will be dictated by its compatability with the particular alcohol being oxidized.

Instead of sodium periodate other alkali metal periodates can be substituted. Likewise, instead of the sodium ruthenate and sodium hydroxide, the corresponding potassium salts and hydroxides of other alkali metals may be used.

While the examples above are concerned chiefly with oxidation of chrysanthemyl alcohol, it is apparent that the invention is applicable to a wide variety of saturated or unsaturated primary or secondary alcohols (absent an interfering functional group, such as NH$_2$). Examples of other alcohols oxidized in accordance with the invention are illustrated below:

EXAMPLE 6

To a stirred suspension of 20 g (94 m mol) sodium periodate in 200 cc of 1 molar sodium hydroxide there was added 0.1 g (0.75 m mol) ruthenium dioxide and 4.32 g (40 m mol) benzyl alcohol. After two hours the reaction was stopped. The mixture was then filtered and the filtrate washed with ether obtaining a neutral fraction comprising benzaldehyde and unreacted benzyl alcohol. The aqueous alkali phase was acidified with sulfuric acid and extracted with ether. There was obtained 4.32 grams of benzoic acid (89% yield).

EXAMPLE 7

To a stirred suspension of 10 g (47 m mol) sodium periodate in 200 cc of 1 molar sodium hydroxide there was added 0.1 g (0.75 m mol) ruthenium dioxide and 4 g (40 m mol) cyclohexanol. After one hour the reaction was stopped. The mixture was filtered and extracted with ether, obtaining 3.3 grams of a neutral material consisting of cyclohexanone (75% yield) and about 9% of the starting alcohol.

EXAMPLE 8

To 4.3 g (40 m mol) benzyl alcohol in 200 cc commercial Chlorox® (5.25% NaOCl) containing 8 g (200 m mol) of additional NaOH, there was added 100 mg (0.75 m mol) $RuO_2$. Within a few minutes a small exotherm was observed. After 1.2 hours the reaction was stopped and the reaction mixture filtered and extracted with ether. The ether extracts were dried ($MgSO_4$) and the solvent removed, obtaining 10 mg benzaldehyde. The aqueous phase was acidified with 15% aqueous $H_2SO_4$, extracted with ether and the ether extracts dried ($MgSO_4$). After removal of the solvent there was obtained 4.7 grams of benzoic acid (96% yield) having a melting point of 120°–121° C.

EXAMPLE 9

2.9 grams (40 m mol) of crotonyl alcohol were added to 1 molar aqueous NaOH (30 grams alcohol/liter of alkaline solution) containing 18 grams of sodium periodate (84 m mol) and 0.1 grams (0.75 m mol) ruthenium dioxide. An orange-red mixture was obtained.

After stirring the obtained mixture for 15 hours at room temperature, it turned black. The mixture was filtered and the pH adjusted to 9 with HCl. The excess water was removed in vacuo, and the residual aqueous solution was further acidified to a pH of 2.

The aqueous alkali phase was then extracted several times with ether. There was obtained 1.9 grams of crude, semi-solid carboxylic acid product in 55% yield. This 1.9 grams of crude product was eluted with chloroform through 10 gm of silica gel, which yielded 1.5 grams of pure crotonic acid.

EXAMPLE 10

To 4.1 grams (24 m mol) of 10-undecenyl alcohol and 120 cc of 1 molar aqueous NaOH were added 10.8 grams (50 m mol) $NaIO_4$ and 0.06 grams of $RuO_2$.

After stirring the resulting mixture for 20 hours at room temperature, the reaction mixture was filtered, acidified to a pH of 2 and extracted with ether. After drying the ether extracts, the ether was evaporated to yield 0.9 grams of 10-undecenoic acid, 71% yield based on an alcohol conversion of 22%.

What is claimed:

1. Process for the oxidation of a primary unsaturated alcohol to its corresponding carboxylic acid wherein said primary alcohol is
    (a) an olefinically unsaturated alcohol selected from the group consisting of straight chain alcohols, branched chain alcohols, and cycloalkyl containing alcohols; or
    (b) an aromatically unsaturated alcohol which contains an aryl alkyl functionality, which comprises contacting the same with a catalytic quantity of a ruthenium catalyst from the group consisting of $RuO_2$ and $A_2RuO_4$ wherein A is an alkali metal cation in an amount of up to about 10 mols of said catalyst per 100 mols of said alcohol in an aqueous alkaline medium and with a substantially stoichiometric amount of an oxidizing agent selected from the group consisting of an alkali metal (per) halate and an alkali metal hypohalite to continually regenerate the $A_2RuO_4$ oxidation catalyst throughout the oxidation reaction.

2. Process according to claim 1 wherein chrysanthemyl alcohol is oxidized at least in part to chrysanthemic acid.

3. Process according to claim 2 wherein the oxidizing agent comprises $NaIO_4$ and the catalyst comprises $RuO_2$.

4. Process according to claim 2 wherein the oxidizing agent comprises $NaIO_4$ and the catalyst comprises $Na_2RuO_4$.

5. Process for the oxidation of chrysanthemyl alcohol to chrysanthemic acid which comprises contacting the alcohol in aqueous alkaline medium with a catalytic quantity of $RuO_2$ in an amount of up to about 10 mols per 100 mols of said alcohol and sodium periodate in substantially stoichiometric quantity to continually regenerate $A_2RuO_4$ oxidation catalyst throughout the oxidation reaction wherein A is an alkali metal cation.

6. The process according to claim 5 wherein chrysanthemyl aldehyde, formed as by product in the oxidation, is subsequently converted by further oxidation to further quantities of chrysanthemic acid.

* * * * *